US006990377B2

(12) United States Patent
Gliner et al.

(10) Patent No.: US 6,990,377 B2
(45) Date of Patent: Jan. 24, 2006

(54) SYSTEMS AND METHODS FOR FACILITATING AND/OR EFFECTUATING DEVELOPMENT, REHABILITATION, RESTORATION, AND/OR RECOVERY OF VISUAL FUNCTION THROUGH NEURAL STIMULATION

(75) Inventors: Bradford E. Gliner, Sammamish, WA (US); Warren D. Sheffield, Seattle, WA (US)

(73) Assignee: Northstar Neuroscience, Inc., Seattle, WA (US)

( * ) Notice: Subject to any disclaimer, the term of this patent is extended or adjusted under 35 U.S.C. 154(b) by 0 days.

(21) Appl. No.: 10/832,477

(22) Filed: Apr. 26, 2004

(65) Prior Publication Data

US 2005/0004624 A1     Jan. 6, 2005

Related U.S. Application Data

(60) Provisional application No. 60/465,671, filed on Apr. 24, 2003.

(51) Int. Cl.
*A61N 1/10* (2006.01)
(52) U.S. Cl. ...................................... 607/54
(58) Field of Classification Search ............... 607/46, 607/53, 54; 600/546, 558; 623/24
See application file for complete search history.

(56) References Cited

U.S. PATENT DOCUMENTS

| | | | |
|---|---|---|---|
| 2,721,316 A * | 10/1955 | Shaw | 607/54 |
| 3,628,193 A * | 12/1971 | Collins | 623/24 |
| 3,650,276 A | 3/1972 | Burghele et al. | |
| 4,140,133 A | 2/1979 | Kastrubin et al. | |
| 4,431,000 A | 2/1984 | Butler et al. | |
| 4,474,186 A * | 10/1984 | Ledley et al. | 600/546 |
| 4,542,752 A | 9/1985 | DeHaan | |
| 4,607,639 A | 8/1986 | Tanagho | |
| 4,646,744 A | 3/1987 | Capel | |
| 4,844,075 A | 7/1989 | Liss | |
| 4,865,048 A | 9/1989 | Eckerson | |
| 5,002,053 A | 3/1991 | Garcia-Rill | |
| 5,031,618 A | 7/1991 | Mullett | |
| 5,054,906 A | 10/1991 | Lyons | |
| 5,092,835 A | 3/1992 | Schurig | |
| 5,143,089 A | 9/1992 | Alt | |
| 5,169,384 A | 12/1992 | Bosniak | |
| 5,215,086 A | 6/1993 | Terry | |
| 5,224,491 A | 7/1993 | Mehra | |
| 5,255,678 A | 10/1993 | Deslauriers | |
| 5,263,967 A | 11/1993 | Lyons | |

(Continued)

FOREIGN PATENT DOCUMENTS

EP          0 998 958 A2    10/2000

(Continued)

OTHER PUBLICATIONS

U.S. Appl. No. 60/325,872, Sheffield.

(Continued)

*Primary Examiner*—George Manuel
(74) *Attorney, Agent, or Firm*—Perkins Coie LLP

(57) ABSTRACT

System and methods for effectuating and/or facilitating visual function in a patient. One embodiment of a system comprises a neural stimulation system and a visual training system. The neural stimulation system can include a pulse generator and a stimulus delivery device coupled to the pulse generator. The stimulus delivery device is configured to deliver a stimulus to the brain of the patient. The visual training system can include a computer and a display coupled to the computer. The computer has a computer operable medium containing instructions to provide a visual output to the patient via the display.

46 Claims, 3 Drawing Sheets

U.S. PATENT DOCUMENTS

| | | |
|---|---|---|
| 5,304,206 A | 4/1994 | Baker |
| 5,314,458 A | 5/1994 | Najafi |
| 5,358,513 A | 10/1994 | Powell |
| 5,370,672 A | 12/1994 | Fowler |
| 5,411,540 A | 5/1995 | Edell |
| 5,417,719 A | 5/1995 | Hull |
| 5,423,864 A | 6/1995 | Ljungstroem |
| 5,522,864 A * | 6/1996 | Wallace et al. ............... 607/53 |
| 5,537,512 A | 7/1996 | Hsia |
| 5,540,736 A | 7/1996 | Haimovich |
| 5,549,655 A | 8/1996 | Erickson |
| 5,575,813 A | 11/1996 | Edell |
| 5,591,216 A | 1/1997 | Testerman |
| 5,593,432 A | 1/1997 | Crowther et al. |
| 5,628,317 A | 5/1997 | Starkebaum |
| 5,683,422 A | 11/1997 | Rise |
| 5,702,429 A | 12/1997 | King |
| 5,711,316 A | 1/1998 | Elsberry |
| 5,713,922 A | 2/1998 | King |
| 5,713,923 A | 2/1998 | Ward |
| 5,716,377 A | 2/1998 | Rise |
| 5,722,401 A | 3/1998 | Pietroski et al. |
| 5,735,814 A | 4/1998 | Elsberry |
| 5,752,979 A | 5/1998 | Benabid |
| 5,772,591 A | 6/1998 | Cram |
| 5,782,798 A | 7/1998 | Rise |
| 5,792,186 A | 8/1998 | Rise |
| 5,797,970 A | 8/1998 | Pouvreau |
| 5,814,014 A | 9/1998 | Elsberry |
| 5,814,092 A | 9/1998 | King |
| 5,824,021 A | 10/1998 | Rise |
| 5,832,932 A | 11/1998 | Elsberry |
| 5,833,709 A | 11/1998 | Rise |
| 5,843,148 A | 12/1998 | Gijsbers |
| 5,843,150 A | 12/1998 | Dreessen |
| 5,885,976 A | 3/1999 | Sandyk |
| 5,886,769 A | 3/1999 | Zolten |
| 5,893,883 A | 4/1999 | Torgerson |
| 5,904,916 A | 5/1999 | Hirsch |
| 5,913,882 A | 6/1999 | King |
| 5,925,070 A | 7/1999 | King |
| 5,938,688 A | 8/1999 | Schiff |
| 5,938,689 A | 8/1999 | Fischell |
| 5,941,906 A | 8/1999 | Barreras |
| 5,964,794 A | 10/1999 | Bolz |
| 5,975,085 A | 11/1999 | Rise |
| 5,978,702 A | 11/1999 | Ward |
| 5,983,140 A | 11/1999 | Smith |
| 6,006,124 A | 12/1999 | Fischell |
| 6,011,996 A | 1/2000 | Gielen |
| 6,016,449 A | 1/2000 | Fischell |
| 6,018,682 A | 1/2000 | Rise |
| 6,021,352 A | 2/2000 | Christopherson |
| 6,026,326 A | 2/2000 | Bardy |
| 6,042,579 A | 3/2000 | Elsberry |
| 6,052,624 A | 4/2000 | Mann |
| 6,055,456 A | 4/2000 | Gerber |
| 6,057,847 A | 5/2000 | Jenkins |
| 6,058,331 A | 5/2000 | King |
| 6,060,048 A | 5/2000 | Cherksey |
| 6,061,593 A | 5/2000 | Fischell |
| 6,066,163 A | 5/2000 | John |
| 6,104,956 A | 8/2000 | Naritoku |
| 6,104,960 A | 8/2000 | Duysens |
| 6,122,548 A | 9/2000 | Starkebaum |
| 6,126,657 A | 10/2000 | Edwards |
| 6,128,537 A | 10/2000 | Rise |
| 6,128,538 A | 10/2000 | Fischell |
| 6,134,474 A | 10/2000 | Fischell |
| 6,152,143 A | 11/2000 | Edwards |
| 6,161,044 A | 12/2000 | Silverstone |
| 6,161,045 A | 12/2000 | Fischell |
| 6,221,908 B1 | 4/2001 | Kilgard |
| 6,301,493 B1 | 10/2001 | Marro et al. |
| 6,353,754 B1 | 3/2002 | Fischell |
| 6,354,299 B1 | 3/2002 | Fischell |
| 6,360,122 B1 | 3/2002 | Fischell |
| 6,366,813 B1 | 4/2002 | DiLorenzo |
| 6,405,079 B1 | 6/2002 | Ansarinia |
| 6,418,344 B1 | 7/2002 | Rezai |
| 6,427,086 B1 | 7/2002 | Fischell |
| 6,459,936 B2 | 10/2002 | Fischell |
| 6,463,328 B1 | 10/2002 | John |
| 6,464,356 B1 | 10/2002 | Sabel |
| 6,466,822 B1 | 10/2002 | Pless |
| 6,473,568 B2 | 10/2002 | Kashiyama |
| 6,473,639 B1 | 10/2002 | Fischell |
| 6,480,743 B1 | 11/2002 | Kirkpatrick |
| 6,484,059 B2 | 11/2002 | Gielen |
| 6,499,488 B1 | 12/2002 | Hunter |
| 6,505,075 B1 * | 1/2003 | Weiner ....................... 607/46 |
| 6,622,048 B1 | 9/2003 | Mann |
| 6,665,562 B2 | 12/2003 | Gluckman et al. |
| 6,687,525 B2 | 2/2004 | Llinas |
| 6,690,974 B2 | 2/2004 | Archer |
| 6,782,292 B2 | 8/2004 | Whitehurst |
| 6,795,737 B2 | 9/2004 | Gielen et al. |
| 2002/0028072 A1 | 3/2002 | Kashiyama |
| 2002/0077670 A1 | 6/2002 | Archer |
| 2002/0087201 A1 | 7/2002 | Firlik |
| 2002/0091419 A1 | 7/2002 | Firlik |
| 2002/0099412 A1 | 7/2002 | Fischell |
| 2002/0169485 A1 | 11/2002 | Pless |
| 2003/0097161 A1 | 5/2003 | Firlik et al. |
| 2003/0114886 A1 | 6/2003 | Gluckman |
| 2003/0125786 A1 | 7/2003 | Gliner et al. |
| 2003/0130706 A1 | 7/2003 | Sheffield et al. |
| 2003/0149457 A1 | 8/2003 | Tcheng et al. |
| 2003/0187490 A1 | 10/2003 | Gliner |
| 2003/0187491 A1 | 10/2003 | Greenberg et al. |
| 2004/0138550 A1 | 7/2004 | Hartlep |
| 2004/0158298 A1 | 8/2004 | Gliner |
| 2004/0243205 A1 | 12/2004 | Keravel et al. |

FOREIGN PATENT DOCUMENTS

| | | |
|---|---|---|
| EP | 1 145 736 | 10/2001 |
| WO | WO-87/07511 | 12/1987 |
| WO | WO-94/07564 | 4/1994 |
| WO | WO-95/21591 | 8/1995 |
| WO | WO-98/06342 | 2/1998 |
| WO | WO-01/97906 | 12/2001 |
| WO | WO-02/09811 | 2/2002 |
| WO | WO-02/36003 | 5/2002 |
| WO | WO-02/38031 | 5/2002 |
| WO | WO-02/38217 | 5/2002 |
| WO | WO-03/082402 | 3/2003 |
| WO | WO-03/043690 | 5/2003 |

OTHER PUBLICATIONS

U.S. Appl. No. 60/325,978, Gliner.

Bel, S. and Bauer, B.L., "Dorsal Column Stimulation (DCS): Cost to Benefit Analysis," Acta Neurochirurgica, Suppl. 52, pp. 121-123 (1991).

Benabid, A.L. et al, "Chronic electrical stimulation of the ventralis intermedius nucleus of the thalamus as a treatment of movement disorders," J. Neurosurg., Apr. 1997, 86(4); 737; http://www.ncbi.nlm.nih.gov; [accessed Nov. 18, 2003].

Butefisch et al., "Mechanisms of use-dependent plasticity in the human motor cortex," Proc. Natl. Acad. Sci. USA, vol. 97, No. 7, pp. 3661-3665 (Mar. 2000).

Canavero, S. and Paolotti, R., "Extradural Motor Cortex Stimulation afor Advanced Parkinson's Disease: Case Report," Movement Disorders, 15(1):169-171, 2000.

Cincotta et al., "Reorganization of the motor cortex in a patient with congenital hemiparesis and mirror movements," Neurology, vol. 55, pp. 129-131 (2000).

Classen, et al., "Rapid Plasticity of Human Cortical Movement Representation Induced by Practice," The Journal of Neurophysiology, vol. 79, No. 2, pp. 1117-1123 (Feb. 1998).

Cohen et al., "Studies of Neuroplasticity With Transcranial Magnetic Stimulation," The Journal of Clinical Neurophysiology, vol. 15, No. 4 (1998).

Cramer, S.C. and Bastings, E.P., "Mapping clinically relevant plasticity after stroke," Neuropharmacology vol. 19, No. 5, pp. 842-851 (Apr. 2000).

Dam et al., "Effects of Fluoxetine and Maprotilins on Functional Recovery in Poststroke Hemiplegic Patients Undergoing Rehabilitation Therapy," Stroke, vol. 27, No. 7, pp. 1211-1214 (Jul. 1996).

Feys et al., "Value of somatosensory and motor evoked potentials in predicting arm recovery after a stroke," (Oct. 1999).

Franzini et al., "Reversal of thalamic hand syndrome by long-term motor cortex stimulation," Journal of Neurosurgery 93:873-875 (2000).

Gladstone et al., "Enhancing Recovery after Stroke with Noradrenergic Pharmacotherapy: A New Frontier?," Can J. Neurol. Sci., vol. 27, No. 2 (May 2000).

Gordon et al., "Parameters for direct cortical electrical stimulation in the human: histopathologic confirmation," Electroencephalography and clinical Neurophysiology, vol. 75, pp. 371-377 (1990).

Hodge, Jr., C.J. and Boakye, M., "Biological Plasticity: The Future of Science in Neurosurgery," Neurosurgery, vol. 48, No. 1 (Jan. 2001).

Hummel, Friedhelm et al., "Effects of non-invasive cortical stimulation on skilled motor function in chronic stroke," Brain Advance Access, Jan. 5, 2005, pp. 1-10, Brain.

International Search Report for PCT/US04/12762; Applicant: Northstar Neuroscience, Inc.; dated Apr. 6, 2005; 6 pgs.

Kauhanen et al., "Domains and Determinants of Quality of Life After Stroke Caused by Brian Infarction," Arch. Phys. Med. Rehabil., vol. 81, pp. 1541-1546 (Dec. 2000).

Kopell et al., "The Continuing Evolution of Phychiatric Neurosurgery," CNS Spectrums, vol. 5, No. 10, pp. 20-31 (Oct. 2000).

Lang, Nicolas et al., "Preconditioning with Transcranial Direct Current Stimulation Sensitizes the Motor Cortex to Rapid-Rate Transcranial Magnetic Stimulation and Controls the Direction of After-Effects," Biol Psychiatry 2004:56: 634-639, 2004 Society of Biological Psychiatry.

Levy et al., "Functional MRI Evidence of Cortical Reorganization in Upper-Limb Stroke Hemiplegia Treated with Constraint-Induced Movement Therapy," American Journal of Physical Medicine & Rehabilitation, vol. 80, No. 1, pp. 4-7 (2001).

Liepert et al., "Treatment-Induced Cortical Reorganization After Stroke in Humans," Stroke, 31:1210-1216 (2000).

Malenka, R.C. and Nicoll, R.A., "Long-Term Potenetiation—A Decade of Progress?," Neuroscience, vol. 285, No. 5435, Issue of Sep. 17, 1999, pp. 1870-1874.

Martinez et al., "Motor hand recovery after stroke Prognostic yield of early transcranial magnetic stimulation," Electromyography. Clin. Neurophysiology, vol. 39, pp. 405-410 (1999).

Netz et al., "Reorganization of motor output in the non-affected hemisphere after stroke," Brain, 120, pp. 1579-1586 (1997).

Nitsche, M.A. and Paulus, W., "Excitability changes induced in the human motor cortex by weak transcranial direct current stimulation," The Journal of Physiology, vol. 527.3, pp. 663-639 (2000).

Nitsche, Michael A. et al., "Level of action of cathodal DC polarisation induced inhibition of the human motor cortex," Dec. 2, 2002, Clinical Neurophysiology 114 (2003) 600-604.

Nitsche, Michael A., et al. "Facilitation of Implicit Motor Learning by Weak Transcranial Direct Current Stimulation of the Primary Motor Cortex in the Human," Journal of Cognitive Neuroscience 15:4, pp 619-626, 2003 Massachusetts Institute of Technology.

Oliveri et al., "Paired transcranial magnetic stimulation protocols reveal a pattern of inhibition and facilitation in the human parietal cortex," The Journal of Physiology, 529.2, pp. 461-468 (2000).

Pascual-Leone et al., "Study and Modulation of Human Cortical Excitability With Transcranial Magnetic Stimulation," Journal of Clinical Neurophysiology, vol. 15, No. 4 (1998).

Pascual-Leone et al., "Transcranial magnetic stimulation and neuroplasticity," Neurophycologia 37, pp. 207-217 (1999).

Paulus, W, "Supplements to Clinical Neurophysiology," Transcranial Magnetic Stimulation and Transcranial Direct Current Stimulation (Supplements to Clinical Neurophysiology; vol. 56), pp 249-254, 2003 Elsevier Science, B.V.

Rezai, "Neurostimulation," Neurological Research, vol. 22, No. 3 pp. 235-273 (Apr. 2000).

Rossi et al., "Effects of Repetitive Transcranial Magnetic Stimulation on Movement-related Cortical Activity in Humans," Cerebral Cortex, vol. 10, No. 8, pp. 802-808 (Aug. 2000).

Roux et al., "Chronic Motor Cortex Stimulation for Phantom Limb Pain: A Functional Magnetic Resonance Imagining Study: Technical Cast Report," Neurosurgery, vol. 49, No. 3 (Mar. 2001).

Saitou et al., "Cerebral Blood Volume and Oxygenation Among Poststroke Hemiplegic Patients: Effects of 13 Rehabilitation Tasks Measured by Near-Infrared Spectroscopy," Arch. Phys. Med. Rehabil., vol. 81 pp. 1348-1356 (Oct. 2000).

Sandkuhler, "Learning and memory in pain pathways," Pain 88, pp. 113-118 (2000).

Sanes, "The Relation between Human Brain Activity and Hand Movements," NeuroImage 11, pp. 370-374 (2000).

Sanes, J. and Donoghue, J.P., "Plasticity and Primary Motor Cortex," Annual Review of Neuroscience 23:393-415 (2000).

Schiff et al., "A neuromodulation strategy for rational therapy of complex brain in injury states," Neurological Research, vol. 22 pp. 267-272 (Apr. 2000).

Shimizu et al., "Therapeutic efficacy of transcranial magnetic stimulation for hereditary spinocerebellar degeneration," Tohoku Journal of Experimental Medicine, 189(3):203-11 (Nov. 1999).

Siebner et al., "Lasting cortical activation after repetitive TMS of the motor cortex," Neurology 54, pp. 956-963 (Feb. 2000).

Stefan et al., "Introduction of plasticity in the human motor cortex by paired associative stimulation," Brian, vol. 123, No. 3, pp. 575-584 (Mar. 2000).

Turton et al., "Contralateral and ipsilateral EMG responses to transcranial magnetic stimulation during recovery of arm and hand function after stroke," Electroencephalography and Clinical Neurophysiology 101 pp. 316-328 (1996).

Turton, A. and Lemon, R.N., "The contribution of fast corticospinal input to the voluntary activation of proximal muscles in normal subjects and in stroke patients," Exp. Brain Res., vol. 129, pp. 559-572 (1999).

Van Der Lee et al., "The Intra- and Interrater Realiability of the Action Research Arm Test A Practical Test of Upper Extremity Function in Patients with Stroke," Arch. Phys. Med Rehabil., vol. 82, pp. 14-19 (Jan. 2001).

Walker-Batson et al., "Amphetamine Paired With Physical Therapy Accelerates Motor Recovery After Stroke," Stroke, vol. 26, No. 12, pp. 2254-2259 (1995).

Ziemann et al., "Modulation of Plasticity in Human Motor Cortex after Forearm Ischemic Nerve Block," The Journal of Neuroscience 18(3):1115-1123 (Feb. 1998).

* cited by examiner

I. OPTIC NERVE (NERVUS OPTICUS)
II. OPTIC CHIASM (CHIASMA OPTICUM)
III. OPTIC TRACT (TRACTUS OPTICUS)
IV. LATERAL GENICULATE NUCLEUS (CORPUS GENICULATUM LATERALE)
V. OPTIC RADIATION (RADIATIO OPTICA)
VI. VISUAL CORTEX (AREA STRIATA)

SYSTEMS AND METHODS FOR FACILITATING AND/OR EFFECTUATING DEVELOPMENT, REHABILITATION, RESTORATION, AND/OR RECOVERY OF VISUAL FUNCTION THROUGH NEURAL STIMULATION

CROSS-REFERENCE TO RELATED APPLICATIONS

This application claims benefit to U.S. Provisional Application No. 60/465,671, filed Apr. 24, 2003.

TECHNICAL FIELD

The present disclosure relates generally to systems and methods for affecting, altering, developing, rehabilitating and/or restoring a visual function of a patient. More particularly, the present disclosure describes systems and methods for addressing visual function in patients by stimulating neural tissue associated with conveying and/or processing visual information.

BACKGROUND

Many problems or abnormalities with body functions can be caused by damage, disease, disorders, and/or developmental difficulties in the brain. For example, strokes are generally caused by emboli (e.g., obstruction of a vessel), hemorrhages (e.g., rupture of a vessel), or thrombi (e.g., clotting) in the vascular system of a specific region of the brain. These events generally cause a loss or impairment of neural function. Other abnormalities are caused by chemical imbalances that affect specific regions of the brain.

A wide variety of mental and/or physical processes are controlled or influenced by neural activity in particular regions of the brain. Several mental and/or physical processes generally correspond or "map" to one or more relatively discrete neural populations within the brain such that the brain exhibits a functional organization according to the cognitive and/or physical processes controlled by the relatively discrete neural populations. The particular regions of the brain that control given types of functions are also generally consistent from one group of individuals to another. In the majority of people, for example, the regions of the left interior frontal lobes relate to language. As another example, particular regions of the cerebral cortex appear to be consistently involved with conscious awareness, memory, and intellect. As shown in FIGS. 1A and 1B, the neural regions associated with the human vision system include the optic nerve, the optic chiasm, the optic tract, the lateral geniculate nucleus, the optic radiation, and the occipital lobes (i.e., the visual cortex/center).

Neurological disorders, disease, and/or damage may impair neural activity within one or more neural populations. This typically results in deterioration and/or loss of physical and/or cognitive abilities associated with the affected neural populations. Thus, as a result of neurological disease or damage, one or more neural populations and/or portions of an individual's neurofunctional map may become impaired, dysfunctional, or essentially nonfunctional. Damage, disease, and/or disorders in the brain resulting from, for example, stroke, traumatic brain injury, or other causes may give rise to various types of visual disorders. Such visual disorders may result in partial blindness or visual field defects such as tunnel vision, hemianopia, quadrantanopia, and/or scotoma.

Effectively treating neurological abnormalities has traditionally been very difficult. For example, physical therapy treatments for stroke patients either alone or in combination with drug treatments fail to significantly improve the function of an affected body part beyond the generally limited recovery that occurs naturally without intervention. As a result, many types of physical and/or cognitive deficits that remain after treating neurological damage or disorders are typically considered permanent conditions that patients must manage for the remainder of their lives.

As an individual acquires a new physical capability, a new memory, or learns or perfects an ability or skill, the extent to which this capability, memory, or skill is functionally represented or implemented by neural connections within particular regions of the brain strengthens or increases. For example, as a guitar player becomes increasingly proficient over time, the number and/or strength of neural connections within the motor cortex directed toward controlling fine finger movements increases. The ability of the brain to structurally adapt in a manner that facilitates neurofunctional map organization, expansion, and/or reorganization is referred to as neuroplasticity.

For patients having certain types of visual field deficits, specific types of vision training may stabilize, improve or enhance visual function. Such stabilization or improvement may result from neuroplastic change or reorganization in vision-related neural populations. U.S. Pat. No. 6,464,356 (see also www.novavision.info), which is incorporated herein by reference, describes a system and technique for improving visual function through selective application of optical stimuli to a patient's visual system. The system and methods described in U.S. Pat. No. 6,464,356 may increase the likelihood of influencing or affecting neurons capable of undergoing neuroplastic change.

Neural activity in the brain can also be affected by electrical or magnetic energy supplied from a waveform generator or other type of device. Various patient perceptions and/or neural functions may be promoted or disrupted by delivering an electrical or magnetic stimulation signal to the brain. A need exists for a neural stimulation system and method that is capable of enhancing or maximizing a likelihood of developing, stabilizing, restoring, and/or rehabilitating visual function on a long term or permanent basis.

DESCRIPTION

The following disclosure describes various systems and methods for providing neural stimulation to one or more neural populations associated with conveying, processing, and/or interpreting visual information. Such systems and methods may facilitate or effectuate neural function stabilization, development, or recovery in individuals having a visual deficit resulting from a developmental disorder, a neurodegenerative disorder, aging, stroke, traumatic brain injury, lesion of the central nervous system, and/or one or more other causes.

The neural stimulation may comprise electrical and/or magnetic stimulation signals, and may comprise alternating (e.g., pulse sequences or trains) and/or direct current (e.g., transcranial Direct Current Stimulation (tDCS)) signals depending upon embodiment details. The neural stimulation may be directed to a set of target neural populations in an affected hemisphere and/or an unaffected hemisphere directly or indirectly involved in development or recovery of visual function. The electrical and/or magnetic signals may be provided or delivered in a continuous or nearly continuous manner, periodically at prescribed time intervals or schedules, or intermittently as needed. Additionally, the neural stimulation may be provided or delivered in conjunction with visual therapy or visual training either simultaneously, essentially simultaneously, temporally overlapping, or sequentially. The neural stimulation may normally delivered below an intensity level at which a patient can detect a sensation (i.e., at a subthreshold level), but it may be desirable to briefly deliver stimulation at levels that cause a detectable, noticeable, and/or measurable patient sensation to enhance a recovery process and/or determine a therapeutic stimulation level.

Figure 1A:
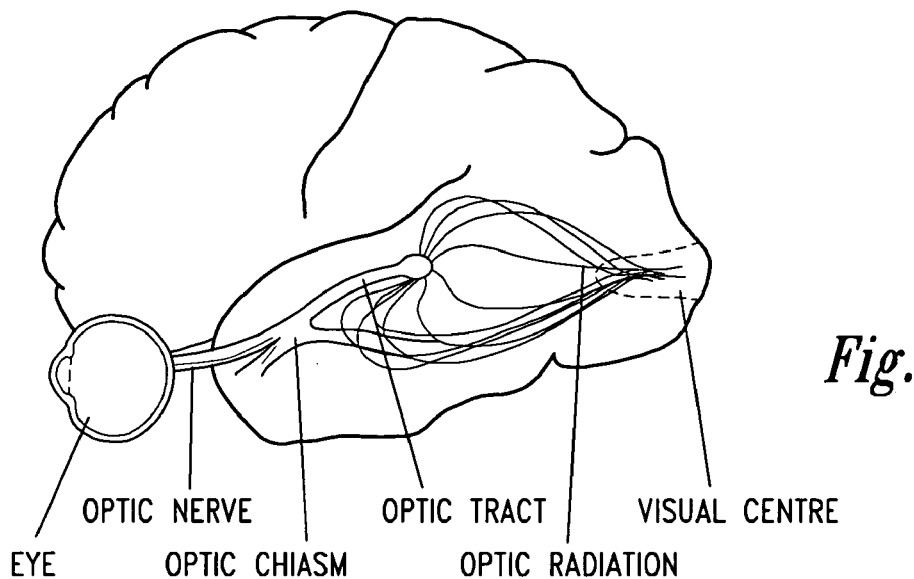
FIGS. 1A and 1B are a schematic illustration of the human visual system.
Figure 1B:
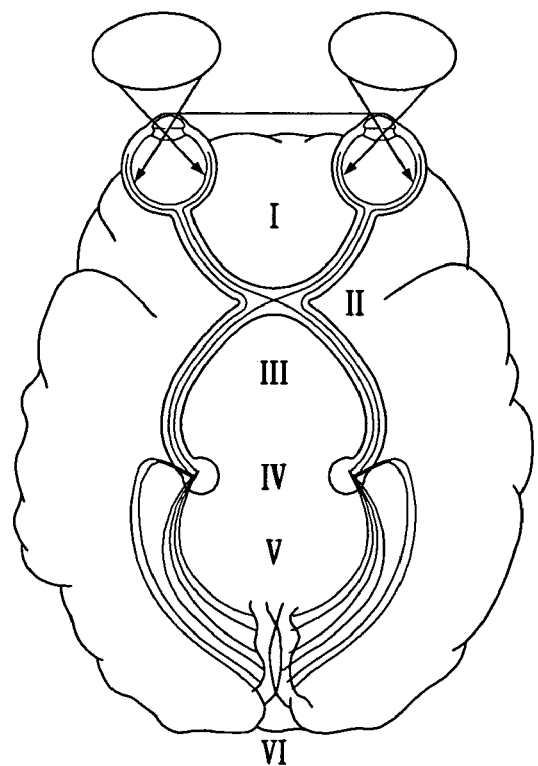
Figure 2:
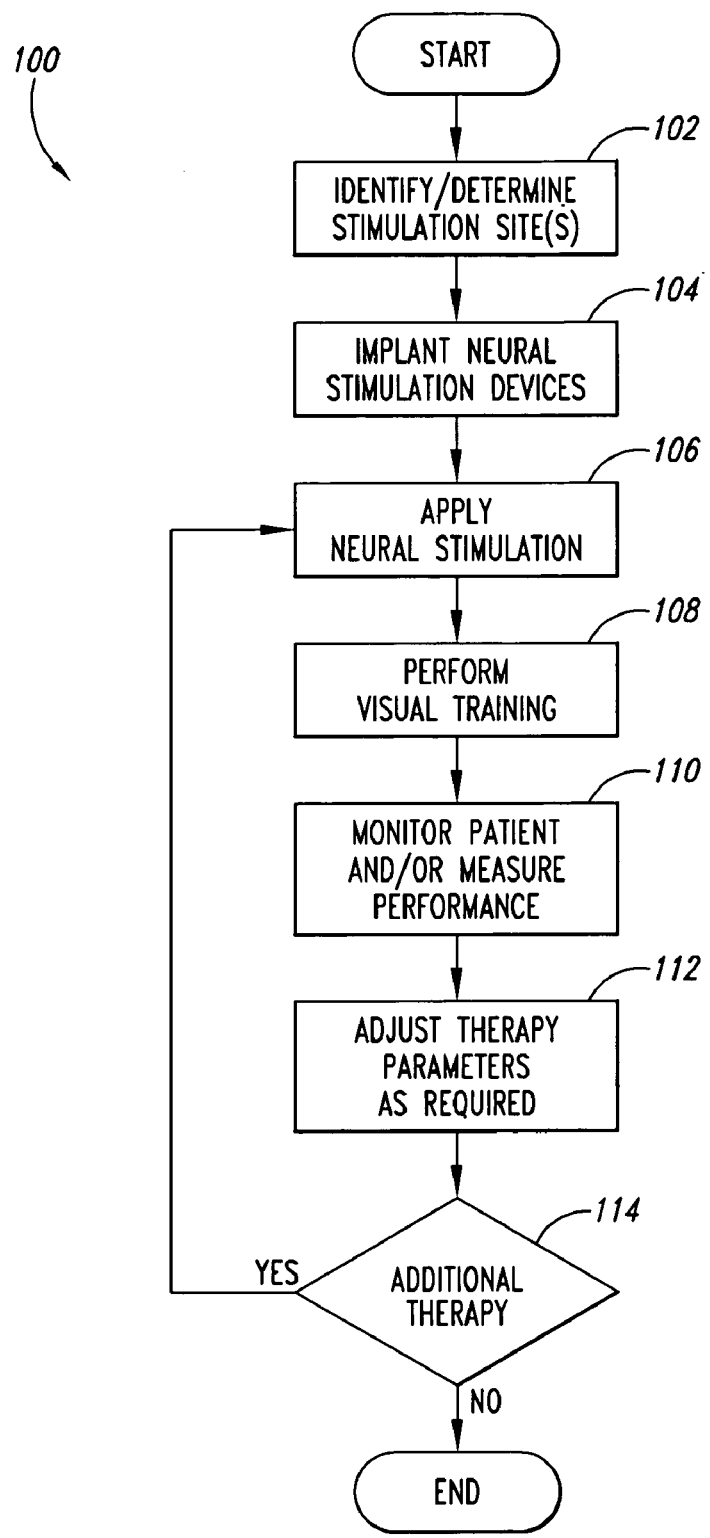
FIG. 2 is a flowchart showing various methods for facilitating and/or effectuating development, rehabilitation, restoration, and/or recovery of visual function through neural stimulation according to an embodiment of the invention.

FIG. 2 is a flowchart illustrating various methods 100 for facilitating and/or effectuating development, rehabilitation, restoration, and/or recovery of visual function through neural stimulation according to an embodiment of the invention. In one embodiment, the method 100 includes an identification procedure 102 for indicating, determining, or identifying one or more neural stimulation sites in a patient. A set of neural stimulation sites may correspond to one or more portions of, for example, the patient's occipital cortex, temporal cortex, parietal cortex, motor cortex, one or more other neural regions, structures, tracts, and/or projections. The identification procedure 102 may involve the use of anatomical landmarks, electrophysiological signal measurement procedures, and/or neural imaging procedures to determine (a) particular target neural populations at which neuroplasticity is occurring or may be expected to occur, and/or (b) target neural populations having neural connections or projections that may be capable of influencing neural activity associated with visual function activity and/or recovery. The identification procedure 102 may indicate a set of stimulation sites and/or neural populations that correspond to healthy and/or impaired visual function.

An electrophysiological signal measurement procedure may involve the measurement, acquisition, generation, and/or calculation of electrophysiological and/or electrophysiologically related signals that may be useful for characterizing neural pathways, neural signal propagation, and/or neural activity associated with the receipt, conveyance, and/or processing of visual information. An electrophysiological signal measurement procedure may utilize evoked potential (EP) and/or evoked field (EF), electroencephalography (EEG), electrocorticography (ECoG), electrooculography (EOG), electroretinography (ERG), sonography (e.g., Doppler and/or velocity coded duplex sonography), cerebral blood flow (CBF), electromyography (EMG), and/or other types of systems and/or techniques. Visual stimuli or optical stimulation may be applied or delivered (for example, using a display device) to the patient in association with an electrophysiological signal measurement procedure. The optical stimulation may comprise, for example, one or more intensity, color, and/or shading patterns (e.g., a time varying checkerboard type pattern and/or a visual motion pattern).

An electrophysiological signal measurement procedure may also involve the measurement or generation of coherence and/or partial coherence signals. In some embodiments, an electrophysiological signal measurement procedure may also involve neural stimulation, for example, Transcranial Magnetic Stimulation (TMS).

Neural imaging procedures may include Positron Emission Tomography (PET), Magnetic Resonance Imaging (MRI), functional MRI (fMRI), Diffusion Tensor Imaging (DTI), and/or other systems and/or techniques. In one embodiment, optical stimulation may be applied to the patient and/or the patient may perform a set of visual tasks while undergoing an fMRI procedure to identify neural populations associated with conveying and/or processing visual information in a manner analogous to certain stimulation site identification procedures described in U.S. patent application Ser. No. 09/802,808, which is incorporated by reference in its entirety. The optical stimulation may comprise flashes of light, one or more optical patterns; and/or other visually perceptible images or information delivered using a set of optical fibers, a headset having a display, a heads-up display projection, and/or a display device. The optical stimulation may also include visual tasks, such as reading, distinguishing colors, etc. The optical stimulation and/or performance of visual tasks may involve the use of an unaffected eye and/or an affected eye. Moreover, the types of optical stimulation applied and/or visual tasks required may depend upon the number, severity and/or nature of the patient's visual deficits or disorders.

In certain embodiments, the method 100 may optionally include an implantation procedure 104 that involves surgically implanting a set of neural stimulation electrodes in the patient. The type and number of neural stimulation electrodes required or desired may vary in accordance with the number, severity, and/or nature of the patient's visual deficits or disorders. Additional factors used to determine the type and number of electrodes include the location and/or nature of the stimulation sites, and/or the target neural populations identified and/or selected during the identification procedure 102. The set of electrodes can include one or more cortical stimulation electrodes, one or more deep brain stimulation electrodes, and/or one or more nerve stimulation electrodes (e.g., nerve cuff electrodes). In certain embodiments, the set of electrodes may include one or more transcranial electrodes. The implantation procedure 104 can also include positioning one or more current return path electrodes upon or within the patient's body. In several embodiments, the implantation procedure 104 includes surgically implanting a pulse generator or pulse generation system or device in the patient, and coupling electrodes to the pulse generator. The pulse generator can have an electrically active housing or case to provide an electrode for one or more electrical current paths. In certain embodiments, one or more electrodes and a pulse generator may form a single, integrated unit.

The method 100 also includes a neural stimulation procedure 106 comprising delivering electrical and/or magnetic stimulation signals to one or more stimulation sites determined by the identification procedure 102. Depending upon the symptoms and other parameters of a specific patient, the neural stimulation procedure 106 may involve cortical, deep brain, and/or cranial nerve stimulation. Suitable cortical stimulation processes may be performed in a manner identical or analogous to those described in U.S. patent application Ser. No. 09/802,808. Deep brain stimulation may be performed in a manner analogous to that described in U.S. Pat. No. 5,833,709 incorporated herein by reference; and cranial nerve stimulation may be performed in a manner identical or analogous to that described in U.S. Pat. No. 6,104,956 also incorporated herein by reference. In certain embodiments, the neural stimulation procedure 106 may involve tDCS, in a manner analogous to that described in "Transcranial Direct Current Stimulation," W. Paulus, *Transcranial Magnetic Stimulation and Transcranial Direct Current Stimulation* (Supplements to *Clinical Neurophysiology*, Vol. 56).

The neural stimulation procedure 106 may alternatively or additionally involve TMS provided or delivered via a conventional TMS system that includes a manually or automatically positionable stimulation coil arrangement (see, for example, www.magstim.com). The TMS system may have at least one magnetic coil positioned within or upon a helmet or other type of headgear, in a manner identical, essentially identical, or analogous to that described in U.S. Pat. No. 6,402,678, which is herein incorporated by reference. The headgear that carries a magnetic coil arrangement may include structural and/or functional elements that facilitate multiple positional adjustments of the magnetic coil arrangement. The magnetic stimulation signals are delivered to one or more neural populations associated with visual function development and/or recovery by activating the magnetic coil arrangement when it is at a location corresponding to at least one stimulation site determined by the identification procedure 102.

The neural stimulation may be delivered in accordance with one or more neural stimulation programs having program instructions that a neural stimulation controller or programming device can communicate to a pulse generation system or stimulation device. Communication between a neural stimulation controller and a pulse generation system may be wire-based or wireless.

The neural stimulation programs may specify delivery of neural stimulation signals or waveforms continuously or at prescribed times in accordance with stimulation parameters that set the phase, current level or intensity, duty cycle, frequency, pulse width and/or other waveform characteristics either statically or dynamically. The stimulation parameters may further specify a) polarities or relative biasing potentials, and/or b) manners in which stimulation waveforms are spatially and/or temporally delivered for particular electrodes or conductive elements. In certain embodiments, some or all of the stimulation parameters may have values that vary as a function of time in either a predetermined, quasi-random, or a periodic manner. Suitable stimulation parameters are set forth in U.S. patent application Ser. No. 09/802,808, but the stimulation parameters may be outside or otherwise different than the ranges set forth therein.

The method 100 may additionally include a visual stimulation and/or visual training procedure 108 comprising the application of visual stimulation and/or performing, attempting to perform, and/or thinking about performing one or more patient activities or behaviors associated with development, enhancement, or recovery of visual function. The visual stimulation and/or training procedure 108 can be performed before, while, and/or after delivering or applying neural stimulation during the neural stimulation procedure 106 described above. Such patient activities or behaviors may be facilitated, directed, or effectuated through a visual training system, which may be implemented using a computer or information processing device having a display device coupled thereto, such as described in U.S. Pat. No. 6,464,356 incorporated by reference above. The visual training system may be configured to be responsive to patient input received via a pointing device, a keyboard, a touch or pressure sensitive pad, a microphone, and/or another type of input device. Additionally, the visual training system may include a head positioning and/or stabilizing apparatus, and a wire-based or wireless link or device that facilitates communication between the visual training system and the neural stimulation controller or programmer.

In one embodiment of the visual stimulation and/or training procedure 108, the patient visually focuses upon a fixation object displayed at a given location for a particular period of time. In another embodiment, optical stimulation may be delivered or applied to particular regions of one or both of the patient's eyes during one or more portions of a visual training procedure 108 in addition to or in lieu of focusing on the fixation object. For example, optical stimulation may be delivered to visual field zones corresponding to reduced, limited, or residual visual function. During the visual training procedure 108, the fixation object may be adjusted, modified, and/or relocated for subsequent patient focusing and/or optical stimulation therapy. The visual training procedure 108 may alternatively or additionally involve an eye movement task, a reading task, a color perception task, a spatial resolution perception task, and/or other tasks.

The method 100 may further include a patient monitoring procedure 110 that involves monitoring, measuring, determining, indicating and/or estimating an extent of visual function performance, visual field change or improvement, neurologic change, and/or neurologic function or dysfunction during or following one or more neural stimulation and/or visual training sessions. In some embodiments, a computer or other device programmed to perform one or more portions of the visual training procedure 108 may also be programmed to implement one or more portions of the monitoring procedure 110. The monitoring procedure 110 can include recording responses from the patient, where such responses may be conveyed and/or received via an input device that the patient operates. Certain embodiments of the monitoring procedure 110 may involve one or more electrophysiological signal measurement and/or neural imaging procedures. Electrophysiological and/or neural imaging signals and/or information derived from or based upon such signals may be compared and/or otherwise processed relative to corresponding earlier acquired and/or reference information to indicate and/or estimate a current patient state or condition.

The method 100 may also include a stimulation adjustment procedure 112 comprising modifying one or more stimulation parameters, visual training parameters and/or visual therapies to enhance or increase recovery or enhancement of visual function. Such adjustments or modifications may be based upon results determined by or in conjunction with the monitoring procedure 110. The adjustment procedure 112 may involve manual or automatic adjustment of neural stimulation and/or visual training parameters. Adjustment of neural stimulation parameters may be carried out in a manner analogous to that described in U.S. patent application Ser. No. 09/978,134, which is incorporated herein by reference.

The method 100 may additionally include an evaluation procedure 114 that involves determining whether the patient requires or would likely benefit from additional neural stimulation therapy and/or visual training sessions. If so, the method 100 may return to the neural stimulation procedure 106 and/or the visual training procedure 108, either immediately or following an elapsed time interval. Such a time interval may span minutes, hours, days, weeks, months, or longer. The evaluation procedure 114 may involve periodically re-evaluating the patient's visual performance and/or visual field following a given time interval and/or a given number of neural stimulation sessions.

Figure 3:
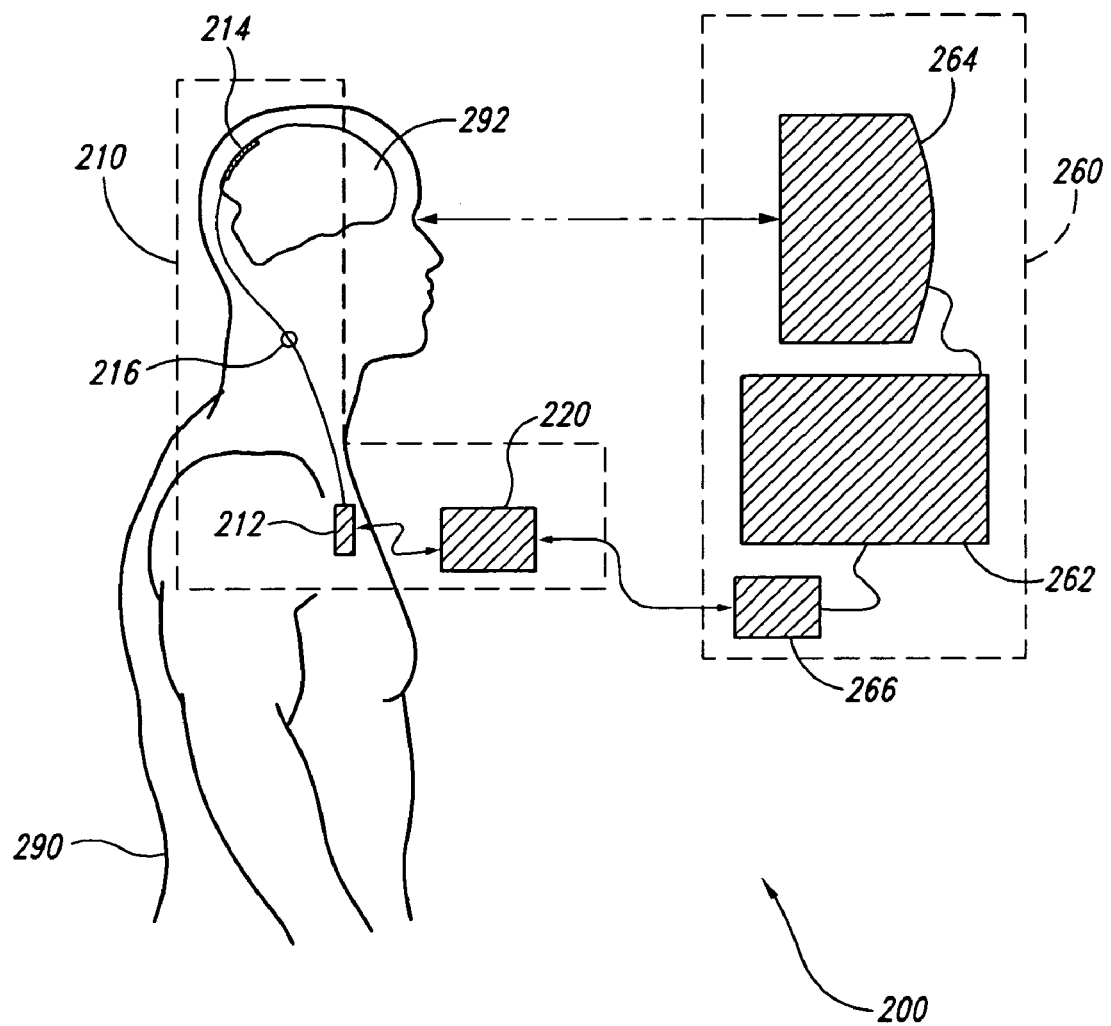
FIG. 3 is a schematic illustration of a neural stimulation and visual training system for facilitating and/or effectuating development, rehabilitation, restoration, and/or recovery of visual function according to an embodiment of the invention.

FIG. 3 is a schematic illustration of a neural stimulation and visual training system 200 for facilitating and/or effectuating development, rehabilitation, restoration, and/or recovery of visual function according to an embodiment of the invention. The system 200 can be configured to perform the embodiments of the method 100 described above. In one embodiment, the system 200 comprises a neural stimulation system 210 and one or more portions of a visual stimulus and/or training system 260. The system 200 may also comprise a patient monitoring unit 290 configured to detect, sense, monitor, measure, generate, and/or calculate patient state signals, which may comprise electrophysiological and/or neural imaging signals. The neural stimulation system 210 may comprise a pulse generator 212, a set of electrodes or an electrode array 214, and one or more leads 216 electrically coupling the pulse generator 212 to the electrode array 214. In this embodiment, the pulse generator 212, the electrode array 214, and the lead 216 are configured to be implanted in a patient 290. The pulse generator, electrode array, or lead, however, may not be implantable in other embodiments. One or more portions of the electrode array 214 are generally positioned relative to a set of target neural populations associated with visual information processing. A suitable location for the electrode array 214 is within the brain 292 at a site where neuroplasticity associated with the development or recovery of the neural function is occurring or is expected to occur. Another suitable location is proximate the dura at the occipital lobes of the cortex of the patient. The neural stimulation system 210 may further include an external controller or programmer 220 configured for wire-based or wireless communication with the pulse generator 212.

The embodiment of the visual stimulus and/or training system 260 shown in FIG. 3 comprises a computer 262 and a display device 264 coupled to the computer 262. The computer 262 includes a processing unit, a programmable medium, and a data storage device. The computer 262 can also have an input device in a manner readily understood by those skilled in the art. The programmable medium may comprise various types of memory, and may store program instructions and data associated with performing visual training therapy in accordance with one or more visual stimulation and/or training procedures 108 of the type described above with reference to FIG. 2. In certain embodiments, the visual training system 260 also includes a communication device 266 coupled to the computer 262 and configured for wire-based or wireless information exchange with the neural stimulation system's controller 220.

From the foregoing, it will be appreciated that particular embodiments of the invention have been described herein for illustrative purposes, but that various modifications may be made without deviating from the spirit and scope of the invention. Accordingly, the invention is not limited by the embodiments described herein.

We claim:

1. A system for effectuating and/or facilitating visual function in a patient, comprising:
   a neural stimulation system including a pulse generator and a stimulus delivery device coupled to the pulse generator, the stimulus delivery device being configured to deliver a stimulus to the brain of the patient via a pathway that does not include the cornea; and
   a visual training system including a computer and a display coupled to the computer, the computer having a computer operable medium containing instructions to provide a visual output to the patient via the display.

2. The system of claim 1 wherein the pulse generator is configured to be subcutaneously implanted into the patient, and wherein the pulse generator comprises an energy storage device and an electrically operable medium containing instructions to generate and deliver an electrical stimulus to the patient.

3. The system of claim 1 wherein the stimulus delivery device comprises a cortical electrode configured to be implanted in the patient at a location proximate to the cortex.

4. The system of claim 1 wherein:
   the stimulus delivery device comprises a cortical electrode configured to be implanted in the patient at a location proximate to the cortex;
   the pulse generator is configured to be implanted into the patient, the pulse generator having an energy storage device and an electrically operable medium containing instructions to generate an electrical pulse; and
   wherein the system further comprises
   a lead electrically coupled to the electrode and the pulse generator to deliver the electrical pulse to the electrode.

5. The system of claim 1 wherein the stimulus delivery device comprises a cortical electrode array including a dielectric carrier and a plurality of electrodes on the dielectric carrier.

6. The system of claim 1 wherein the stimulus delivery device comprises a cortical electrode array including a flexible carrier and a plurality of electrodes on the carrier.

7. The system of claim 1 wherein the stimulus device comprises a deep brain electrode and/or a nerve cuff electrode.

8. The system of claim 1 wherein the computer operable instructions generate a fixation image on the display.

9. The system of claim 1 wherein the computer operable instructions generate a series of images on the display.

10. A method for effectuating and/or facilitating visual function in a patient, comprising:
    identifying a neural stimulation site corresponding to neural activity associated with the visual function, and at which neuroplasticity is occurring and/or may be expected to occur to carry out the visual function; and
    applying neural stimulation to a population of neurons at the stimulation site via a pathway that does not include the cornea.

11. The method of claim 10 wherein:
    applying the neural stimulation comprises implanting a cortical electrode in the patient proximate to the cortex and delivering an electrical stimulus directly to the cortex via the implanted electrode and wherein the method further comprises;
    providing a visual input to the patient for visual training and/or tasking; and
    monitoring a response in the patient.

12. The method of claim 10 wherein identifying a neural stimulation site comprises determining a location of a target population of neurons in the cortex where neuroplasticity is occurring and/or may be expected to occur to carry out the visual function.

13. The method of claim 10 wherein identifying a neural stimulation site comprises imaging neural activity using functional MRI while providing a visual input to the patient and determining a target population of neurons in the cortex associated with the visual function.

14. The method of claim 10 wherein identifying a neural stimulation site comprises selecting at least one of the occipital lobes of the cortex.

15. The method of claim 10 wherein applying stimulation comprises implanting a cortical electrode in the patient proximate to the dura of the cortex and delivering an electrical stimulus directly to the cortex via the implanted electrode.

16. The method of claim 10 wherein applying stimulation comprises delivering an electromagnetic stimulation transcutaneously through the cranium.

17. The method of claim 10, further comprising performing visual training while applying the neural stimulation.

18. The method of claim 17 wherein performing the visual training comprises instructing the patient to visually focus on a fixation object.

19. The method of claim 17 wherein performing the visual training comprises delivering optical stimulation to the patient's eyes.

20. The method of claim 17 wherein performing the visual training comprises delivering optical stimulation to visual field zones corresponding to reduced, limited and/or residual visual function.

21. The method of claim 10 further comprising evaluating patient performance.

22. The method of claim 21 wherein evaluating patient performance comprises receiving feedback from the patient via a computer input device.

23. The method of claim 10 further comprising adjusting a stimulation parameter and reapplying the neural stimulation.

24. A method for effectuating and/or facilitating visual function in a patient, comprising:
    implanting an electrode at an occipital lobe of the patient proximate to the dura of the cortex;
    implanting a pulse generator in the patient and electrically coupling the pulse generator to the electrode; and
    applying electrical pulses to the electrode.

25. The method of claim 24 wherein applying electrical pulses comprises generating a continuous pulse train of pulses.

26. The method of claim 24 further comprising performing visual training while applying the electrical pulses to the electrode.

27. The method of claim 26 wherein performing the visual training comprises instructing the patient to visually focus on a fixation object.

28. The method of claim 26 wherein performing the visual training comprises delivering optical stimulation to the eyes of the patient.

29. The method of claim 26 further comprising adjusting a stimulation parameter and reapplying different electrical pulses to the electrode.

30. A system for effectuating and/or facilitating visual function in a patient, comprising:
    a neural stimulation system including a pulse generator and a stimulus delivery device coupled to the pulse generator, the stimulus delivery device being configured to deliver a stimulus to the brain of the patient, the stimulus delivery device comprising a cortical electrode configured to be implanted in the patient at a location proximate to the cortex; and
    a visual training system including a computer and a display coupled to the computer, the computer having a computer operable medium containing instructions to provide a visual output to the patient via the display.

31. The system of claim 30 wherein the pulse generator is configured to be subcutaneously implanted into the patient, and wherein the pulse generator comprises an energy storage device and an electrically operable medium containing instructions to generate and deliver an electrical stimulus to the patient.

32. The system of claim 30 wherein:
    the pulse generator is configured to be implanted into the patient, the pulse generator having an energy storage device and an electrically operable medium containing instructions to generate an electrical pulse; and
    wherein the system further comprises
    a lead electrically coupled to the electrode and the pulse generator to deliver the electrical pulse to the electrode.

33. The system of claim 30 wherein the stimulus delivery device comprises a cortical electrode array including a dielectric carrier and a plurality of electrodes on the dielectric carrier.

34. The system of claim 30 wherein the stimulus delivery device comprises a cortical electrode array including a flexible carrier and a plurality of electrodes on the carrier.

35. The system of claim 30 wherein the computer operable instructions generate a fixation image on the display.

36. The system of claim 30 wherein the computer operable instructions generate a series of images on the display.

37. A method for effectuating and/or facilitating visual function in a patient, comprising:
    identifying a neural stimulation site corresponding to neural activity associated with the visual function, and at which neuroplasticity is occurring and/or may be expected to occur to carry out the visual function; and
    applying neural stimulation to a population of neurons at the stimulation site by implanting a cortical electrode in the patient and delivering an electrical stimulus to the cortex via the implanted electrode.

38. The method of claim 37 wherein:
    identifying a neural stimulation site comprises determining a location of a target population of neurons in the cortex where neuroplasticity is occurring and/or may be expected to occur to carry out the visual function;
    applying the neural stimulation comprises implanting a cortical electrode in the patient proximate to the cortex and delivering an electrical stimulus directly to the cortex via the implanted electrode;
    providing a visual input to the patient for visual training and/or tasking; and
    monitoring a response in the patient.

39. The method of claim 37 wherein identifying a neural stimulation site comprises determining a location of a target population of neurons in the cortex where neuroplasticity is occurring and/or may be expected to occur to carry out the visual function.

40. The method of claim 37 wherein identifying a neural stimulation site comprises imaging neural activity using functional MRI while providing a visual input to the patient and determining a target population of neurons in the cortex associated with the visual function.

41. The method of claim 37 wherein identifying a neural stimulation site comprises selecting at least one of the occipital lobes of the cortex.

42. The method of claim 37, further comprising performing visual training while applying the neural stimulation.

43. The method of claim 42 wherein performing the visual training comprises instructing the patient to visually focus on a fixation object.

44. The method of claim 42 wherein performing the visual training comprises delivering optical stimulation to the patient's eyes.

45. The method of claim 42 wherein performing the visual training comprises delivering optical stimulation to visual field zones corresponding to reduced, limited and/or residual visual function.

46. The method of claim 37 further comprising adjusting a stimulation parameter and reapplying the neural stimulation.

* * * * *